(12) United States Patent
Di et al.

(10) Patent No.: US 7,060,428 B2
(45) Date of Patent: Jun. 13, 2006

(54) METHODS AND COMPOSITIONS USEFUL FOR THE PREDICTION OF BLOOD-BRAIN BARRIER PERMEATION

(75) Inventors: Li Di, West Windsor, NJ (US); Edward Harvel Kerns, Skillman, NJ (US)

(73) Assignee: Wyeth, Madison, NJ (US)

( * ) Notice: Subject to any disclaimer, the term of this patent is extended or adjusted under 35 U.S.C. 154(b) by 502 days.

(21) Appl. No.: 10/383,335

(22) Filed: Mar. 7, 2003

(65) Prior Publication Data

US 2003/0165813 A1      Sep. 4, 2003

Related U.S. Application Data

(63) Continuation-in-part of application No. 10/185,052, filed on Jun. 28, 2002, now abandoned.

(60) Provisional application No. 60/302,085, filed on Jun. 29, 2001.

(51) Int. Cl.
*C12Q 1/00* (2006.01)
(52) U.S. Cl. .......................................................... 435/4
(58) Field of Classification Search .................... 435/4
See application file for complete search history.

(56) References Cited

U.S. PATENT DOCUMENTS 4,776,173 A * 10/1988 Kamarei et al. ............... 62/63
5,260,210 A    11/1993 Rubin et al.

OTHER PUBLICATIONS

Franke et al. "An improved low-permeability in vitro-model of the blood-brain marrier: transport studies on retinoids, sucrose, haloperidol, caffeine and mannitol" Brain Res. (1999) 818:65-71.*
Millipore Catalog, 1991-1992, pp. 14-15.*
Millipore Website: http://www.millipore.com/catalogue.nsf/docs/C7631.*
Yang et al. "Immobilized artificial membranes—screen for drug membrane interactions" Advanced Drug Delivery Reviews (1996) 23: 229-256.*
Pagliara et al. "Evaluation and prediction of drug permeation" J. Pharm. Pharmacol. (1999) 51: 1339-1357.*
Wohnsland, F. and Faller, B., High-Throughput Permeability of pH Profile and High-Throughput Alkane/Water log P with Artificial Membranes, Journal of Medicinal Chemistry, 2001, 44, 923-930.
Kansy, M.; Senner, F. and Gubernator, K., Physicochemical High Throughput Screening: Parallel Artificial Membrane Permeation Assay in the Description of Passive Absorption Processes, Journal of Medicinal Chemistry, 1998, 41, 1007-1010.
Gumbleton, Mark and Audus, Kenneth L., Journal of Pharmaceutical Sciences, 2001, 90: 1681-1698.

* cited by examiner

*Primary Examiner*—Jean C. Witz
*Assistant Examiner*—Susan Hanley
(74) *Attorney, Agent, or Firm*—Barbara L. Lences

(57) ABSTRACT

The present invention provides a method for the in vitro determination of the ability of a compound or a mixture of compounds to permeate the blood-brain barrier and a membrane composition useful therefor.

15 Claims, No Drawings

METHODS AND COMPOSITIONS USEFUL FOR THE PREDICTION OF BLOOD-BRAIN BARRIER PERMEATION

This application is a continuation-in-part application of application Ser. No. 10/185,052 filed on Jun. 28, 2002, now abandoned and claims the benefit of Provisional Application No. 60/302,085, filed Jun. 29, 2001, the entire disclosure of which is incorporated by reference.

BACKGROUND OF THE INVENTION

To be effective as therapeutic agents, centrally acting pharmaceuticals must cross the blood-brain barrier (BBB). Conversely, to be devoid of unwanted central nervous system (CNS) effects, peripherally acting pharmaceuticals should demonstrate limited ability to cross the BBB. In either case, the BBB permeability of a pharmaceutical candidate needs to be known. However, the experimental determination of blood-brain partitioning is difficult, time-consuming, costly and unsuitable for screening large collections of chemicals. A broadly applicable method for predicting the BBB permeation of pharmaceutical candidates at an early stage of discovery would have a significant impact in pharmaceutical research and development. Methods which produce reliably predictable data related to BBB permeation for large numbers of compounds at an early stage of the discovery/development process are urgently needed.

Therefore, it is an object of this invention to provide a robust, efficient and predictive method for the in vitro determination of the BBB permeation capabilities of a test compound such as a potential pharmaceutical agent.

It is another object of this invention to provide a membrane composition useful for the in vitro determination of the BBB permeation capabilities of a test compound.

It is a feature of this invention that the BBB permeation determinative method and composition provide high predictive value and high throughput efficiency.

It is another feature of this invention that said method and composition are adaptable to standard laboratory robotics platforms.

These and other objects and features of the invention will become more apparent by the detailed description set forth hereinbelow.

SUMMARY OF THE INVENTION

The present invention provides a method for the determination of the ability of a compound or mixture of compounds to permeate the blood-brain barrier which comprises measuring the rate said compound or mixture of compounds passively diffuses through a porous filter membrane impregnated with a mixture of brain polar lipid extract and dodecane.

The present invention further provides a membrane composition which comprises a porous solid support impregnated with a mixture of brain polar lipid extract and dodecane.

DETAILED DESCRIPTION OF THE INVENTION

Methods which can deliver reliable and predictive data related to blood-brain barrier (BBB) permeation for large numbers of compounds, i.e, 500–1,000 per day, at an early stage of the discovery development process would allow the rapid and inexpensive selection and optimization of pharmaceutical candidates for desirable brain penetration characteristics and may help in the differentiation between active, paracellular and transcellular processes. Known methods for predicting BBB penetration include computational methods using mathematical tools, cell culture methods using endothelial cell cultures from animal origin, high performance liquid chromatography (HPLC) using immobilized artificial membrane columns, measurement of surface activity using critical micelle concentration methodology, microdialysis techniques involving sampling tissue from the brain of a living animal for external HPLC analysis, the use of postmortem human brain capillaries, and in vivo animal studies. None of these known methods are entirely suitable for obtaining economic, reliable and highly predictive BBB permeation data for large numbers of test compounds.

Surprisingly, it has now been found that the ability of a compound or a mixture of compounds to permeate the blood-brain barrier may be determined in a highly predictive, reproducible, reliable, efficient and economic manner in vitro by measuring the rate said compound or mixture of compounds passively diffuses through a porous filter membrane impregnated with a mixture of brain polar lipid extract and dodecane. Advantageously, the method of the invention is suitable for use with standard laboratory robotics platforms.

The term passive diffusion, as used in the specification and claims, designates a process of transfer of individual molecules of a compound or mixture of compounds across a semi-permeable membrane which is brought about by random molecular motion and associated with a concentration gradient. The modifier passive refers both to the absence of external forces such as increased pressure, reduced pressure, gravity or the like and to the lack of active processes such as metabolism, the use of transporters or the like.

The inventive method is a simple, high through-put physico-chemical method which uses a very small amount of sample, generally less than 0.1 mg, to accurately predict the ability of said sample to permeate the blood-brain barrier. In actual practice, a solution of known concentration of a compound or mixture of compounds in a buffer solution is separated from a buffer solution containing 0% concentration of said compound or mixture of compounds by a porous filter membrane impregnated with a mixture of brain polar lipid extract and dodecane in such a way that the surface of each buffer solution is in contact with opposite sides of said impregnated membrane. After a measured period of time, the concentration of said compound or mixture of compounds is determined for each buffer solution and the rate of diffusion is calculated.

In one embodiment of the invention, a 96-well plate filled with solutions of a known concentration of test sample in a buffer solution (donor) may be covered with a 96-well filter plate wherein the porous filter membrane is impregnated with a mixture of brain polar lipid extract and dodecane and the wells are filled with a buffer solution containing 0% concentration of test sample (acceptor) such that the surface of each buffer solution is in contact with opposite sides of said impregnated filter membrane; after a measured period of time, the donor plate and acceptor plate are separated, the concentration of sample in each buffer solution is determined and the rate of permeation is calculated.

In another embodiment of the invention, a high through-put permeability instrument such as the PSR4p instrument manufactured by pION Inc., Woburn, Mass. may be utilized. In this embodiment, a parallel artificial membrane assay (PAMPA) technique is employed using as artificial membrane a porous filter membrane impregnated with a mixture of brain polar lipid extract and dodecane.

Buffer solutions suitable for use in the method of invention include any conventional buffer solution of about pH 6.0–8.0, preferably about pH 7.2–7.6 and more preferably about pH 7.4.

Accordingly, the method of the invention demonstrates higher predictability for blood-brain barrier permeability with higher through-put capacity, lower cost and without the sacrifice of living animals than those methods currently known in the art.

The present invention also provides a membrane composition which comprises a porous solid support impregnated with a mixture of brain polar lipid extract and dodecane. The mixture of brain polar lipid extract and dodecane suitable for use in the inventive composition may be about 1.0% wt/vol to 3.0% wt/vol, preferably about 1.5% wt/vol to 2.5% wt/vol, more preferably about 1.9% wt/vol to 2.1% wt/vol of brain polar lipid extract in dodecane, particularly preferably about 2.0% wt/vol of brain polarlipid extract in dodecane.

A porous solid support suitable for use in the inventive composition includes any commonly used porous material such as that used in the 96-well filter plates, for example polyvinylideneflouride or an equivalent thereof, preferably polyvinylideneflouride.

Brain polar lipid extracts suitable for use in the composition of the invention may be those brain polar lipid extracts, either synthetic or natural, which can be found in the literature or which are commercially available such as porcine, ovine, bovine or the like, preferably porcine brain polar lipid extract.

The composition of the invention may be prepared by impregnating the porous solid support with a mixture of brain polar lipid extract and dodecane at a level of at least 4 µL/38 mm$^2$, preferably about 4 µL/38 mm$^2$, of said mixture per area of porous solid support.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

EXAMPLE 1

Comparative Evaluation of the Predictability for Blood Brain Barrier Permeability of the Inventive Method Using Known Compounds In this evaluation, 30 literature compounds for which the blood-brain barrier permeability is known (P. Crivari, et al, Journal of Medicinal Chemistry, 2000, 43, 2204–2216) are each dissolved in DMSO at a concentration of 5 mg/mL to give a stock solution for each compound. A 100 µL volume of each stock solution is placed into one well of a 96-well plate, and the well plate is placed in a PSR4p permeability analyzer manufactured by pION, Inc., Woburn, Mass. A 10 µL volume of stock solution is robotically added to a deep 96-well plate containing 2.0 mL of pH 7.4 buffer solution. The resultant mixture is mechanically stirred to form the donor solution. A 200 µL volume of each donor solution is placed robotically into 3 wells of a 96-well plate to afford the donor plate. A vial containing 20 mg of porcine polar brain lipid extract manufactured by Avanti Polar Lipids, Inc., Alabaster, Ala., dissolved in 1 mL of dodecane is placed in the reservoir of the PSR4p instrument. A 4 µL volume of this brain lipid solution is placed on the filter surface of each well of a 96-well microtiter filter well plate manufactured by Millipore Corp., Bedford, Mass., wherein the the filter is a porous (0.45 µm) polyvinylidenefluoride material approximately 104 µm in thickness. The microtiter plate is then manually placed on an orbital shaker for 1 minute to yield a 96-well microtiter plate having a filter membrane permeated with a 2.0% wt/vol solution of porcine polar brain lipid extract in dodecane. A 200 µL volume of pH 7.4 buffer is robotically inserted into the wells of the thus-prepared microtiter 96-well filter plate to give a receptor plate, this receptor plate is placed on the donor plate to form a sandwich and allowed to stand at ambient temperature for 18 h.

A plate washer manufactured by Tecan, Hombrechintikon, Switzerland is then used to prepare a UV transparent 96-well plate (UV plate). The receptor plate is removed from the sandwich, a 150 µL volume of the receptor solution is robotically placed in the UV plate, and the UV absorption at 190–500 nm of each receptor well is recorded. The UV plate is then replaced in the plate washer, washed again and a 150 µL volume of the donor solution is robotically placed in the UV plate and the UV absorption at 190–500 nm of each donor well is recorded. The rate of passive diffusion is measured as linear velocity of permeation (Pe). The Pe is calculated for each compound using version V1.4 of the PSR4p software from pION Inc. Two standards, verapamil and theophylline, are used for each microtiter plate. BBB permeability is designated as CNS+ for Pe values $\geq 4\times10^{-6}$ cm/sec and as CNS– for Pe values $\leq 2\times10^{-6}$ cm/sec. The data are averaged and the results are shown in Table I.

TABLE I

| Test Compound | Pe ($10^{-6}$ cm/s) | CNS Eval | Known[2] |
|---|---|---|---|
| Alprazolam | 5.44 | + | + |
| Caffeine[1] | 1.30 | – | + |
| Chlorpromazine | 6.36 | + | + |
| Clobazam | 16.85 | + | + |
| Clonidine | 5.31 | + | + |
| Desipramine | 11.89 | + | + |
| Diazepam | 16.41 | + | + |
| beta-Estradiol | 11.61 | + | + |
| Imipramine | 13.12 | + | + |
| Oxazepam | 10.12 | + | + |
| Progesterone | 9.28 | + | + |
| Promazine | 8.84 | + | + |
| Testosterone | 16.75 | + | + |
| Thiopental | 18.13 | + | + |
| Aldosterone | 1.19 | – | – |
| Astemizole[1] | 10.66 | + | – |
| Atenolol | 0.84 | – | – |
| Hydrocortisone | 1.99 | – | – |
| Dopamine | 0.16 | – | – |
| Enoxin | 0.90 | – | – |
| Isoxicam | 0.25 | – | – |
| Lomefloxacin | 1.19 | – | – |
| Loperamide | 0.00 | – | – |
| Corticosterone[1] | 5.13 | + | – |
| Norfloxacin | 0.14 | – | – |
| Ofloxacin | 0.80 | – | – |
| Piroxicam | 2.53 | – | – |
| Terfenadine | 0.00 | – | – |
| Tenoxicam | 0.14 | – | – |
| Cimetidine | 0.00 | – | – |

[1]These compounds were involved in active processes, i.e., carrier mediated transport (caffeine), Pgp efflux (corticosterone) and rapid metabolism (astemizole).
[2]Crivori, P., et al., Journal of Medicinal Chemistry, 2000, 43, 2204–2216.

As can be seen by the data on Table I, the inventive method demonstrates 90% accuracy for all 30 test compounds including active transport processes. For passive diffusion, the inventive method demonstrates 100% accuracy.

EXAMPLE 2

Comparative Evaluation of the Predictability for Blood Brain Barrier Permeability of the Inventive Method Using Experimental Compounds Using essentially the same procedure described in Example 1 and substituting experimental compounds obtained from three separate CNS projects, the Pe values are determined and compared to the blood-brain barrier permeability as determined by standard rat brain assay methodology or biological endpoints from in vivo studies. The results are shown in Table II.

TABLE II

| Test Compound | Pe ($10^{-6}$ cm/s) | CNS Eval | CNS In vivo |
| --- | --- | --- | --- |
| A | 6.52 | + | + |
| B | 6.07 | + | + |
| C | 18.99 | + | + |
| D | 11.61 | + | + |
| E | 9.68 | + | + |
| F | 10.62 | + | + |
| G | 15.11 | + | + |
| H | 5.20 | + | + |
| I | 13.75 | + | + |
| J | 0.40 | − | − |
| K | 0.13 | − | − |
| L | 0.05 | − | − |
| M | 0.03 | − | − |
| N | 0.08 | − | − |

As can be seen from the data on Table II, the inventive method demonstrates 100% accuracy.

What is claimed is:

1. A method for the determination of the ability of a compound or mixture of compounds to permeate the blood-brain barrier which comprises measuring the rate said compound or mixture of compounds passively diffuses through a porous filter membrane impregnated with a mixture of brain polar lipid extract and dodecane.

2. The method according to claim 1 wherein said extract is porcine brain polar lipid extract.

3. The method according to claim 1 wherein said mixture is about 1.0% wt/vol to 3.0% wt/vol of brain polar lipid extract in dodecane.

4. The method according to claim 1 wherein said impregnated membrane has a thickness of about 100 μm to 150 μm.

5. The method according to claim 1 wherein said filter membrane has a pore size of about 0.45 μm.

6. The method according to claim 5 wherein said filter membrane is a polyvinylidene fluoride filter membrane.

7. The method according to claim 6 wherein said membrane is impregnated with about 4 μL of a mixture of brain polar lipid extract and dodecane per 38 mm$^2$ of membrane.

8. The method according to claim 7 wherein said mixture is about 2.0% wt/vol of porcine brain polar lipid extract in dodecane.

9. The method according to claim 8 wherein said impregnated membrane has a thickness of about 100 μm to 150 μm.

10. A membrane composition which comprises a porous solid support impregnated with a mixture of brain polar lipid extract and dodecane.

11. The composition according to claim 10 wherein said extract is porcine brain polar lipid extract.

12. The composition according to claim 10 wherein said mixture is about 1.0% wt/vol to 3.0% wt/vol brain polar lipid extract is dodecane.

13. The composition according to claim 10 wherein the porous solid support is a polyvinylidene fluoride filter membrane.

14. The composition according to claim 13 wherein said filter membrane is impregnated with at least 4 μL of a 2.0% wt/vol mixture of brain polar lipid extract in dodecane per 38 mm$^2$ of said membrane.

15. The composition according to claim 14 wherein said extract is porcine brain polar lipid extract.

* * * * *